(12) United States Patent
Fenyvesi et al.

(10) Patent No.: US 8,486,458 B2
(45) Date of Patent: Jul. 16, 2013

(54) METHODS AND COMPOSITIONS FOR EXTRACTING FLAVOR AND FRAGRANCE COMPOUNDS AND SOLUBILIZING ESSENTIAL OILS

(75) Inventors: Gyorgyi Fenyvesi, Wilmington, DE (US); Raja Hari Poladi, Bear, DE (US); Hari Babu Sunkara, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 217 days.

(21) Appl. No.: 12/938,452

(22) Filed: Nov. 3, 2010

(65) Prior Publication Data

US 2011/0274630 A1 Nov. 10, 2011

Related U.S. Application Data

(60) Provisional application No. 61/257,866, filed on Nov. 4, 2009.

(51) Int. Cl.
*A61K 36/00* (2006.01)
*A61K 47/00* (2006.01)
*A11B 9/00* (2006.01)

(52) U.S. Cl.
USPC ................................ 424/725; 514/783; 512/5

(58) Field of Classification Search
None
See application file for complete search history.

(56) References Cited

U.S. PATENT DOCUMENTS

| 3,755,560 | A | 8/1973 | Dickert et al. |
| 4,421,769 | A | 12/1983 | Dixon et al. |
| 5,374,614 | A | 12/1994 | Behan et al. |
| 5,633,362 | A | 5/1997 | Nagarajan et al. |
| 5,686,276 | A | 11/1997 | Laffend et al. |
| 5,821,092 | A | 10/1998 | Nagarajan et al. |
| 6,316,586 | B1 | 11/2001 | Sunkara et al. |
| 6,403,109 | B1 | 6/2002 | Stora |
| 6,608,168 | B1 | 8/2003 | Ng |
| 2003/0007939 | A1 | 1/2003 | Murad |
| 2005/0176921 | A1 | 8/2005 | Sunkara et al. |
| 2007/0269392 | A1* | 11/2007 | Sunkara ......................... 424/59 |
| 2008/0108845 | A1 | 5/2008 | Sunkara et al. |

FOREIGN PATENT DOCUMENTS

| JP | 02011520 A | 1/1990 |
| WO | 9718283 A1 | 5/1997 |
| WO | 0033804 A1 | 6/2000 |
| WO | 2004093836 A2 | 11/2004 |
| WO | 2006002249 A1 | 1/2006 |
| WO | 2006043177 A1 | 4/2006 |

* cited by examiner

*Primary Examiner* — Qiuwen Mi

(57) ABSTRACT

Provided are methods for extracting flavor and fragrance materials from natural plant materials, using poly(trimethylene ether) glycol homopolymers and copolymers. The poly(trimethylene ether) glycol homopolymers and copolymers act as solubilizers for essential oils, and can be used to provide compositions having a variety of uses in applications such as cosmetics, personal care products, and industrial cleaning products.

3 Claims, No Drawings

METHODS AND COMPOSITIONS FOR EXTRACTING FLAVOR AND FRAGRANCE COMPOUNDS AND SOLUBILIZING ESSENTIAL OILS

TECHNICAL FIELD

The present invention is directed to methods using polytrimethylene ether glycols for extracting flavor and fragrance materials from natural plant materials and as solubilizers for essential oils, and compositions made by the methods. The present invention is also directed to methods of using polytrimethylene ether glycols as a cleaning agent.

BACKGROUND

Solvents derived from petrochemicals are commonly used to extract flavor and fragrance materials from botanical sources for use in adding aroma to consumer products. Solvents are also used to dissolve essential oils. Environmental, market, esthetic and other factors have recently led to desire on the part of consumers and producers for alternatives to petrochemicals as sources for solvents and other components in a variety of products.

The *"Common Fragrance and Flavor Materials"* (Preparation, Properties and Uses, 5$^{th}$ Ed. Horst Surburg and Johannes Panten Copyright © WILEY-VCH Verlag GmbH & Co. KGaA, Weinheim) discloses methods for the isolation of natural fragrance and flavor concentrates. Major methods used to concentrate flavor and fragrance materials include distillation, mechanical separation and solvent extraction.

Essential oils can be obtained by distillation of plant materials with water or steam. After condensation of the water phase, the water separates from the essential oils. The essential oils can be used directly as starting material for flavors and fragrances or can be highly diluted with certain solvents. Distillates can be obtained by the distillation of plant materials with water-ethyl alcohol mixtures, and the products of the distillation contain ethanol. Alcohol, however, is not desirable for some products, and can cause skin irritants for some individuals. While an aqueous solvent would be desirable, many essential oils and other botanical materials are not water-soluble. There are certain plant materials (e.g. jasmine) for which distillation cannot be used successfully because the heat treatment would deteriorate the aroma materials; therefore solvent extraction is used to obtain flavor and fragrances from such plants.

It is generally desirable to avoid the use of volatile organic compounds (VOC) in products such as personal care products. Also other petrochemical solvents are broadly used for plant extraction as hexane, toluene and petroleum ether. These solvents, though are effective to extract flavor and fragrance materials from plants, but can be difficult to remove completely, and. therefore the final products can contain undesirable odor and harmful or toxic ingredients, and may cause skin irritation or other health related problems.

Water-based microemulsions containing perfumes or flavors, have been developed, as disclosed, for example, in U.S. Pat. No. 6,403,109. However, microemulsions rely on the use of large amounts of surfactants, which also may be undesirable for some consumer products. Silicones, which are also present in the emulsions disclosed in U.S. Pat. No. 6,403,109, may also be undesirable in some products.

A need remains for materials that are non-petroleum based, non-volatile, non-toxic, non-hazardous and biodegradable, and have high efficacy to extract flavor and fragrance materials from plants and to solubilize essential oils and other botanical extracts for use in consumer and industrial products. It is also desirable to have methods that are simple and safe, and eliminate the need for removal of high VOC petroleum based solvents. It is further desirable to be able to use renewably sourced and biodegradable materials in consumer and industrial products containing botanical extracts.

SUMMARY OF THE INVENTION

One aspect of the present invention is a method for extracting essential oil from a plant comprising a) contacting plant material with a composition comprising one or more of poly (trimethylene ether) glycol homopolymer or copolymer, wherein the homopolymer or copolymer has a molecular weight within the range of about 134 to about 2000, to form an extract; and b) isolating the extract from the plant material by filtration.

Another aspect of the present invention is method for solubilizing an essential oil, comprising contacting the essential oil with a composition comprising one or more of poly(trimethylene ether) glycol homopolymer or copolymer, wherein the homopolymer or copolymer has a molecular weight within the range of about 134 to about 2000 to form a solution or microemulsion.

Another aspect of the present invention is an essential oil, a solution or a microemulsion prepared by the above methods, and a personal care or cosmetic formulation thereof.

Another aspect of the present invention is composition comprising an essential oil and one or more of poly(trimethylene ether) glycol homopolymer or copolymer, wherein the homopolymer or copolymer has a molecular weight within the range of about 134 to about 2000, and wherein the composition has a surface tension of at least 38.0.

DETAILED DESCRIPTION

Unless otherwise stated, the following terms as used herein have the following meanings.

An "extractant" is an agent used to isolate or extract desirable substances from natural plant materials An "extract" is a composition obtained from a substance, primarily by chemical or mechanical action. The extract can contain non-volatile as well as volatile components.

A "concrete" is an extraction of fresh natural plant materials obtained with non-polar organic solvents A "tincture" is an ethanol or ethanol-water mixture extraction in which the solvent is left as a diluent.

A "resinoid" is a solid or semi-solid material similar to concrete but prepared from exudates by extraction and purification with a solvent.

"Essential oils" are the volatile, lipophilic substances obtained from plant materials (such as, for example, shrubs, flowers, trees, roots, bark, and seeds) that are mainly hydrocarbons or monofunctional compounds derived from mono- and sesquiterpenes, phenylpropanoids, amino acids and from fatty acids.

A "solubilizer" is an agent used to dissolve essential oils or other botanical extracts "VOC" means the volatile organic compounds A "microemulsion" is a thermodynamically stable colloidal system, wherein the particles have average radii of about 10 nm.

The present invention provides methods and compositions for extracting and solubilizing essential oils of plant sources, or other botanical extracts, such as flavor and fragrance materials, using a polytrimethylene ether glycol as an extractant or solubilizer. In some embodiments, the polytrimethylene ether glycol is renewably sourced.

Polytrimethylene ether glycol is typically prepared by polycondensation of monomers comprising 1,3-propanediol, typically in the presence of an acid catalyst, thus resulting in polymers or copolymers containing a —(CH$_2$CH$_2$CH$_2$O)— linkage (e.g, trimethylene ether repeating units). Typically, at least 50% of the repeating units are trimethylene ether units.

One source of 1,3-propanediol is via a fermentation process using a renewable biological source. As used herein, the term "renewably sourced, when applied to poly(trimethylene ether) glycol homopolymer or copolymer, refers to poly(trimethylene ether) glycol homopolymer or copolymer made from 1,3-propanediol derived from a renewable biological source. As an illustrative example, biochemical routes to 1,3-propanediol (PDO) are known in the art that utilize feedstocks produced from biological and renewable resources such as corn feed stock. For example, bacterial strains able to convert glycerol into 1,3-propanediol are found in the species *Klebsiella*, *Citrobacter*, *Clostridium*, and *Lactobacillus*. The technique is disclosed in several patents, including U.S. Pat. Nos. 5,633,362, 5,686,276 and 5,821,092 (the disclosures of which are incorporated by reference herein for all purposes as if fully set forth). For example, U.S. Pat. No. 5,821,092 discloses, inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, the processes disclosed in these publications provide a rapid, inexpensive and environmentally responsible source of 1,3-propanediol monomer.

Essential oils useful as flavor and fragrance materials in the methods and compositions disclosed herein can be obtained from any plants, trees, algae, fungi or can be synthesized in a laboratory. Various parts of the plant material can be extracted, such as, for example, leaves, roots, stems, buds, twigs, rhizomes, heartwood, bark, resin, flowers, seeds, fruits or, in some embodiments, the entire plant. Examples of suitable plant families can include: Anacardiaceae Araceae, Balanopaceae, Balsaminaceae, Begoniaceae, Boraginaceae, Buxaceae, Caricaceae, Cucurbitaceae, Clusiaceae, Daphniphyllaceae, Ericaceae, Euphorbiaceae, Fabaceae, Fagaceae, Hippocastanaceae, Hostaceae, Hydrangeaceae, Labiateae, Lilaeaceae, Magnoliaceae, Moringaceae, Myristicaceae, Myrtaceae, Oleaceae, Orchidaceae, Peperomiaceae, Pinaceae, Primulaceae, Rutaceae. Specific examples of plant and tree species include: *Achillea millefolium, Aesculus chinensis, Allium sativum, Artemisia apiacea, Astrocaryum murumuru, Bactris gasipaes, Benincasa hispida, Celastrus paniculatus, Cetraria islandica, Chenopodium quinoa, Cinchona succirubra, Citrus bergamia, Citrus reticulata, Citrus sinensis, Coriandrum sativum, Codium tomentosum, Commiphora molmol, Crataegus cuneata, Cucumis sativus, Eucalyptus globulus, Gleditsia sinensis, Gnetum amazonicum, Hibiscus rosa-sinensis, Jasminum officinale, Lonicera caprifolium, Lonicera japonica, Lycopersicon esculentum, Malus pumila, Matricaria recutita, Maximiliana maripa, Melaleuca hypericifolia, Melaphis chinensis, Mentha piperita, Mouriri apiranga, Nasturtium officinale, Nelumbo nucifera, Oenothera biennis, Ophiopogon japonicus, Persea americana, Paffia paniculata, Phellodendron amurense, Phyllanthus emblica, Pisum sativum, Potentilla erecta, Pterocarpus santalinus, Rehmannia chinensis, Ribes nigrum, Rosa centifolia, Rubus thunbergii, Saccharomyces cerevisiae, Spondias amara, Styrax benzoin,* and *Thymus vulgaris.*

Families of algae from which aroma materials can be obtained include: Acrochaeticaceae, Characeae, Codiaceae, Fucaceae, Laminariaceae, Lemaneaceae, Ulvaceae, Pamariaceae. Specific examples of algae species from which essential oils can be obtained include: *Lemanea fluviatilis* (red algea), (L.), *Ascophyllum nodosum* (brown alga), *Lemanea fluviatilis, Lemanea fucina* (red algea), *Ulva lactuca* (green alga), *Laminaria digitata, Laminaria ochroleuca.*

Aroma materials can also be obtained from fungi, including classes of Homobasidiomycetes (true mushrooms). Mushroom families suitable as sources for essential oils include Meripilaceae, Tricholomataceae, Ganodermataceae (maitake, shiitake, reishi mushrooms). Mushroom species for essential oils include *Agaricus bisporus, Agaricus campestris, Flammulina velutipes Hypsizygus tessulatus, Lentinus edodes, Phellinus linteus, Pleurotus cornucopiae, Pleurotus ostreatus, Tremella fuciformis, Sparassis crispa, Tuber magnatum, Volvariella volvacea.*

The essential oils are typically water insoluble. Essential oils contain volatile and lipophilic substances and are mainly derivatives of mono- and sesquiterpenes, phenylpropanoids, amino acids and long chain fatty acids. Naturally-occurring essential oils can be blended with synthetic fragrances and the term "essential oils" is intended to encompass such blends.

The methods and compositions disclosed herein can be used for making concretes and tinctures by extracting flavor and fragrance materials from natural plant materials using a polytrimethylene ether glycol as an extractant. The compositions can be used following extraction without further treatment. In some embodiments, the polytrimethylene ether glycol is renewably sourced.

Examples of naturally-occurring essential oils include: Basil, benzoin, bergamot, black pepper, cajuput, chamomile, camphor, caraway, carrot seed, *cassia*, cedar wood, cinnamon, citronella, clove, coriander, cypress, dill, eucalyptus, fennel, geranium, ginger, grapefruit, jasmine, juniper, lavender, lemon, lemongrass, lime, mandarin, marjoram, myrrh, nutmeg, orange, peppermint, rose, sage, spearmint, sandalwood, tangerine, thyme, tea tree, and ylang ylang.

The polytrimethylene ether glycols suitable for use in the methods and compositions disclosed herein as an extractant or as a solubilizer, have several advantages. For example, the polytrimethylene ether glycols are non-volatile, generally non-toxic, non-hazardous, materials which can be renewably sourced. "Renewably sourced", as used herein with regard to the polytrimethylene ether glycols, means that they are made using a renewably sourced ingredient, 1,3-propanediol. The present inventors surprisingly discovered the high efficacy of the polytrimethylene ether glycols as extractants to remove flavor and fragrance materials from natural plant based materials and also as solubilizers for essential oils. Renewably sourced polytrimethylene ether glycols thus can replace petroleum based materials in such applications, which is desirable for many consumer and personal care products.

The solubility of a substance (solute) in a solvent is generally determined by the balance of intermolecular forces between the solvent and solute. Solvents with relatively higher intermolecular forces have relatively high surface tension and relatively higher values of solubility parameter, and vice-versa. The attractive interaction energy of the solvent molecules must match the attractive intermolecular energy in the solute in order to form a solution. The surface tension is a measure of the inward force acting on the surface of a liquid due to the attraction of molecules in the liquid. Polyethylene glycol (300 MW), with a surface tension of 45.9 dynes/cm, is crystalline, viscous and polar in nature due to higher intermolecular forces, whereas polypropylene glycol (425 MW), with a surface tension of 32.9 dynes/cm, is a low viscosity liquid, amorphous and non-polar in nature. Therefore, polyethylene glycol is used to solubilize polar solutes and polypropylene glycol is used to solubilize non-polar solutes. The surface tension value for polytrimethylene ether glycol, on the other hand, is 42.7 dynes/cm for 250 MW polymer and 40.7 dynes/cm for 650 MW polymer, significantly higher than its isomer, polypropylene glycol, 32.9 dynes/cm for 425 MW polymer, in spite of having same number of carbon and oxygen atoms in the backbone. The surface tension value for polytrimethylene ether glycol is close to the hydrophilic polyethylene glycol suggesting that it could be used in a same way as polyethylene glycol. Surprisingly however, the solubilizing efficacy of polytrimethylene ether glycol for essential oils is unpredictable, and shows greater solubility than polyethylene glycol, 1,3-propanediol or polypropylene glycol.

Suitable polytrimethylene ether glycols for use in the methods disclosed herein are polytrimethylene ether glycol homopolymers and copolymers of relatively low molecular weight, and esters (mono-, diesters and mixtures thereof) of the polytrimethylene ether glycols. In general, the non-polarity of the polyether molecules increases with increase in molecular weight and therefore, a desirable molecular weight can be selected based on the materials to be extracted or solubilized. "Low molecular weight" as used herein, means that typically the polymers have a number average molecular weight within the range of 134 to 2000. More typically the polymers have a number average molecular weight less than 1000 or within the range of 250 to 1000, and in some embodiments the polymers have a number average molecular weight less than about 650, or within the range of 250 to 650. In another embodiment the polymers have a number average molecular weight less than about 250. Suitable polymers are commercially available, such as, for example, Cerenol® H650 polytrimethylene ether glycol, available from E. I. du Pont de Nemours and Company, Wilmington, Del., or can be prepared as disclosed in U.S. Pat. No. 7,074,969.

Suitable copolymers include poly(trimethylene ether ester) glycols such as those disclosed in U.S. Pat. Nos. 6,316, 586 and 6,608,168, and poly (trimethylene-co-ethylene ether) glycol, such as disclosed in U.S. Patent Publication No. 2005/0176921. Suitable esters of polytrimethylene ether glycols are disclosed in U.S. Patent Application No. 2009/108845.

In preparing concrete compositions according to the methods disclosed herein, polytrimethylene ether glycol of desired number average molecular weight is used to extract essential components of the natural plant materials first by mixing both materials, allowing sufficient time to dissolve, and by removing the non-essential components that are not dissolved. The mixing of the polyether glycol and plant material is done at room temperature or at slightly elevated temperature and the separation of residual materials from the extract is done by filtration. The extract (tincture) rendered can be further diluted with polytrimethylene ether glycol or any other desired solvent and can be used in various formulations. If desired, the volatile flavor and fragrance materials can be isolated from the extract by distillation at atmospheric pressure or reduced pressure. The polytrimethylene ether glycol polymers exhibit desirable solubility characteristics for many natural plant materials and can used without further purification in cosmetic, personal care, pharmaceutical or industrial applications.

Generally, tinctures are prepared by treating the plant materials with ethanol or ethanol-water mixtures. Polytrimethylene ether glycols, typically having a number average molecular weight in the range of 134 to 650, or mixtures of such polytrimethylene ether glycols and water, are suitable to obtain tinctures of plant materials.

Polytrimethylene ether glycols and esters (aliphatic, aromatic or branched) of polytrimethylene ether glycols are also very effective in dissolving the essential oil extracts of plant sources, and can be used as solubilizers. Clear and homogeneous solutions can be obtained by dissolving high concentrations of essential oil in polytrimethylene ether glycol. In preparing solutions, a polytrimethylene ether glycol having a desired number average molecular weight is mixed with a desired essential oil or other botanical extract at room temperature or slightly at elevated temperature. The clarity of the solutions can be measured by turbidity as a function of time and it is expressed in nephelometric turbidity units (NTU). The NTU of the compositions is 100 or lower, typically 60 or lower, and desirably 40 or lower. In some embodiments, the compositions are substantially free of VOCs.

Compositions containing solubilized essential oils according to the methods disclosed herein can be used include cosmetic and personal care formulations such as decorative cosmetics (eye creams, foundations, lipsticks, glosses), hair care (shampoos, conditioners, hair gels, hair lotions and tonics), perfumes and fragrances (colognes, toilet waters, perfumes), skin care (baby care, body care, facial care, facial cleansing creams and lotions), sun care (sun protection, after-sun and self tanning formulations) and toiletries (antiperspirants and deodorants, depilators, hand wash formulations, shower and bath formulations). The solubilized essential oil compositions can be used for industrial applications, such as cleansers, detergents (laundry detergents, dishwashing detergents), fabric softeners, and also for textile treatments.

The method used for solubilizing an essential oil, comprising contacting the essential oil with a composition comprising one or more of poly(trimethylene ether) glycol homopolymer or copolymer can also be used to prepare aqueous solutions, emulsions or microemulsions by further adding water and surfactant(s). Surfactants, which include emulsifiers, are compounds that have hydrophobic and hydrophilic portions that act to reduce the surface tension of the aqueous solutions in which they are dissolved. Essential oils are in general water immiscible and in order to make water based compositions, stable emulsions or microemulsions can be used, but typically require large amounts of surfactant(s). However, it has been found that solutions containing essential oils dissolved in polytrimethylene ether glycol are dispersible in water and therefore it is expected that clear and transparent microemulsions from such solutions can be obtained with reduced amounts of surfactant(s) as compared to conventional emulsions and microemulsions. Solutions of ester (mono and diester or mixture of esters) of polytrimethylene ether glycol and essential oils can be used in oil-in-water, water-in-oil or multiple emulsions or other types of cosmetic, pharmaceutical or industrial formulations. Examples of suitable surfactants are disclosed in US2003/0007939A1, U.S. Pat. Nos. 3,755,560 and 4,421,769.

The amount of water added depends on the desired end use but typically is up to about 80 percent by weight, or 50 percent, or 30 percent, or 10 percent based on the total weight of the solution or microemulsion.

In some embodiments, the compositions can contain less than 10 percent by weight of total surfactants, more typically less than 5 percent, less than 2 percent, less than 1 percent, or less than 0.5 percent. However, surfactants can be added to the solution after solubilization, for use in certain formulations such as moisturizing creams or other formulations containing ingredients that are not readily soluble in the polyether glycols.

In some embodiments, the compositions are substantially silicone free. Silicones, as used herein, refer broadly to linear and cyclic silicones and siloxanes, including those referred to in the art as dimethicone, cyclomethicone, etc. Although volatile silicone fluids (i.e., silicone fluids having a vapor pressure at room temperature equal to or greater than that of ethanol) can be used in a variety of personal care and cosmetic formulations, and such formulations are not intended to be excluded for making products from the solutions disclosed herein, such products are not required in making solutions having desired clarity.

Poly(trimethylene ether) glycol homopolymer or copolymer can also be used by itself as a cleaning agent to remove polar lipophilic soils such as adhesives, oils, or fats in industrial applications where solvents with lower surface tension do not function well. Poly(trimethylene ether) glycol homopolymer or copolymer can also be used as a cosolvent with water, alcohol, glycol ether and ketones, and as a component of cleansers, detergents (laundry detergents, dishwashing detergents), fabric softeners, and also for textile treatments.

In other embodiments, essential oils, solutions or microemulsions can prepared by the methods disclosed herein, and personal care or cosmetic formulations comprising the essential oil, solution or microemulsion.

In some embodiments, a composition can be prepared comprising essential oil and one or more of poly(trimethylene ether) glycol homopolymer or copolymer, wherein the homopolymer or copolymer has a number average molecular weight within the range of about 134 to about 2000, and wherein the composition has a surface tension of at least 38.0, or at least 40.0. The composition can also have a turbidity of less than 60 nephelometric turbidity units. The poly(trimethylene ether) glycol homopolymer or copolymer are as described above. More typically the polymers have a number average molecular weight less than 1000 or within the range of 250 to 1000, and most typically the polymers have a number average molecular weight less than about 650 or within the range of 250 to 650. In another embodiment the polymers have a number average molecular weight less than about 250.

The compositions can be used in personal care or cosmetic formulations, or as disclosed hereinabove, as a component of cleansers, detergents (laundry detergents, dishwashing detergents), fabric softeners, and also for textile treatments. The compositions can be in the form of a solution or microemulsion, which can be neat or aqueous. They can also contain added water or surfactants. The amount of water added depends on the desired end use but typically be up to about 80 percent by weight, or 50 percent, or 30 percent, or 10 percent of the solution or microemulsion.

In some embodiments, the compositions can contain less than 10 percent by weight of total surfactants, more typically less than 5 percent, less than 2 percent, less than 1 percent, or less than 0.5 percent. However, surfactants can be added to the solution after solubilization, for use in certain formulations such as moisturizing creams or other formulations containing ingredients that are not readily soluble in the polyether glycols. In some embodiments, the compositions are substantially silicone free.

EXAMPLES

The meaning of the abbreviations used in the examples is as follows: "s" means second(s), "min" means minute(s), "h" means hour(s), "kg" means kilogram(s), "g" means gram(s), "mg" means milligram(s), "µg" means microgram(s), "oz" means ounce(s), "yd" means yard(s), "mmol" means millimole(s), "m" means meter(s), "cm" means centimeter(s), "mm" means millimeter(s), "µm" means micrometer(s), "mL" means milliliter(s), "µL" means microliter(s), "M" means molar, "N" means normal, "wt %" means weight percent, "ppm" means parts per million, "MW" means molecular weight, "$M_n$" means number average molecular weight, "$M_w$" means weight average molecular weight. Unless otherwise specified, any water used is distilled or deionized water.

Number average molecular weights (Mn) of the polytrimethylene ether glycols were determined by end-group analysis using NMR spectroscopic methods. Turbidity measurements on the solubiized compositions were carried out using a nephelometric turbidimeter (MicroTPW, Model 20000, Scientific Inc. FT. Myers, Fla.) monitors light reflected off the suspended particles. The NTU (Nephelometric Turbidity Unit) numbers represent the transparency of a solution; the lower numbers represent higher transparency. Surface tension was measured for neat glycols and glycols containing essential oils by ring (DuNouy) method using Cahn dynamic contact angle analyzer (model DCA-312).

Polytrimethylene ether glycol having Mn 250 and 500 were prepared as disclosed in U.S. Pat. No. 7,074,969. Polytrimethylene ether glycol having Mn 650 (Cerenol® H650) was obtained from E. I. du Pont de Nemours and Company, Wilmington, Del. Plant materials were obtained from Mountaine Rose Herbs, Eugene, Oreg.

The biodegradability of low molecular weight polytrimethylene ether glycols were tested according to the guidelines shown in Table 1 and the results are presented in Table 1.

TABLE 1

| Molecular weight of polytrimethylene ether glycol | Test method | Biodegradation |
| --- | --- | --- |
| 250 | OECD 301 B | 66% in 28 days |
| 500 | OECD 302B | 93% in 28 days |

Examples 1-8 and Comparative Examples 1-3

The Examples 1-8 and Comparative examples 1-3 were all prepared using the following procedure. The plant materials were mixed with 50 g of polytrimethylene ether glycol in a glass jar and placed on a shaking table, then the mixture was shaken for 72 hours. The plant material was filtered by gravity filtration and the filtrate physical properties were recorded. The results are is shown in Table 2.

TABLE 2

Physical properties of the extracts

| | Plant | Polytrimethylene ether glycol (Mn) | Physical appearance Color | Odor character |
|---|---|---|---|---|
| Example | | | | |
| 1 | Jasmine (dried flower), 10 g | 250 | Yellow, transparent | Mild |
| 5 | Myrrh (gum), 10 g | 650 | Dark brown | Strong, woody |
| 6 | Lavender (dried flower), 10 g | 650 | Light brown, transparent | Pleasant, woody |
| 7 | Chamomile (powder), 5 g | 650 | Yellow, transparent | Mild |
| 8 | Jasmine (dried flower), 10 g | 650 | Yellow | Mild |
| 6 | Myrrh (gum), 10 g | | | |
| 1 | Jasmine (dried flower), 10 g | 650 | Colorless, transparent | Mild, grass |
| 2 | Chamomile (powder), 5 g | 650 | Yellow | Mild |
| Comparative Example | | | | |
| 1 | Jasmine (dried flower), 10 g | Hexane | Colorless, transparent | Mild, grass |
| 2 | Myrrh (resinoid), 10 g | Hexane | Colorless, transparent | Mild, grass |
| 3 | Lavender (dried flower), 10 g | Ethanol | Green, transparent | Pleasant, herbaceous |

As shown, the physical appearance (deep color), and the odor character (strong herbaceous smell) of the products clearly demonstrate that the renewably sourced polytrimethylene ether glycol polymers can be successfully replace petrochemicals for plant extraction and can provide safer, high purity materials, which can be used in cosmetic, personal care, pharmaceutical or in industrial applications even without further purification and expensive and tedious removal of the solvent/s.

Example 9

Surface Tension of Liquids 0.5 g of essential oil (lavender, Mountaine Rose Herbs, Eugene, Oreg.) was mixed with 9.5 g of glycol. The surface tension of the resulting solutions was compared with neat solvent. The results are shown in Table 3.

TABLE 3

Surface Tension of Neat Solvents and the Mixtures of Essential Oil and Solvent

| | Surface tension (dynes/cm) | |
|---|---|---|
| Sample | Neat Solvent | Solvent + 5% Lavender |
| Lavender | 28.1 | — |
| 1,3-Propanediol | 48.3 | 33.8 |
| Polyethylene glycol-300 MW | 45.9 | 34.4 |
| Polytrimethylene ether glycol-250 MW | 42.7 | 38.9 |

TABLE 3-continued

Surface Tension of Neat Solvents and the Mixtures of Essential Oil and Solvent

| | Surface tension (dynes/cm) | |
|---|---|---|
| Sample | Neat Solvent | Solvent + 5% Lavender |
| Polytrimethylene ether glycol-650 MW | 40.7 | 40.0 |
| Polypropylene glycol-425 MW | 32.9 | 34.3 |

As shown in Table 3, the high surface tension of the liquid solution containing polytrimethylene ether glycol and lavender indicates stronger intermolecular attraction between these two molecules when compared to other glycols. For example, lavender essential oil has a surface tension of 28 dynes/cm and therefore are expected to be less soluble in polar molecules such as, polyethylene glycol and polytrimethylene ether glycol than in non polar molecule such as polypropylene glycol. However, when the lavender is added to the glycols, the surface tension values for all of the resulting solutions are much lower than polytrimethylene ether glycol solution, suggesting high degree of attraction between lavender molecules and polytrimethylene ether glycols.

Examples 10-12

Essential oils of different plant materials were used for testing as detailed below. The essential oils were mixed with 9.5 g (95 wt %) of polytrimethylene ether glycol (Mn=250) and turbidity was recorded periodically. Results are shown in Table 4.

TABLE 4

Turbidity of Essential Oils/Polytrimethylene ether glycol mixtures

| Example | Essential Oil of Plant (g) | Polytrimethylene ether glycol, Mn = 250 (g) | Turbidity @ 0 min (NTU) | Turbidity @ 5 min (NTU) | Turbidity @ 120 min (NTU) | Turbidity @ 300 min (NTU) |
|---|---|---|---|---|---|---|
| 10 | Chamomile, 0.5 | 9.5 | 36.8 | 17.1 | 14.4 | 15.1 |
| 11 | Lavender, 0.5 | 9.5 | 52.6 | 47.1 | 35.8 | 28.4 |
| 12 | Jasmine, 0.5 | 9.5 | 32.9 | 20.4 | 21.0 | 20.3 |

Results in Table 4 demonstrate that polytrimethylene ether glycols are excellent vehicles for the dissolution of essential oils of different plant materials. Low turbidity was observed within short period of time (in some cases after 5 minutes) after gentle mixing of the materials, indicating fast dissolution of the materials.

The results demonstrate that clear solution can be obtained by mixing botanical essential oils with polytrimethylene ether glycol homopolymers. The turbidity dramatically decreased rapidly in case of jasmine and the solution was stable for at least 6 months at room temperature. In Comparative Example 4, phase separation and small particles were visually observed.

Example 13 and Comparative Examples 4-5

0.5 g (5 wt %) of essential oils of different plant materials were used for testing. The essential oils were mixed with 9.5 g (95 wt %) of polytrimethylene ether glycol (Mn=650), hexane (Aldrich), and di-propylene glycol (DPG) (Aldrich), and turbidity was recorded periodically as described above. Results are shown in Table 5.

Examples 14-16

0.5 g (5 wt %) of essential oils were mixed with 9.5 g (95 wt %) of polytrimethylene ether glycol (Mn=250) and other additives, and turbidity was recorded periodically and viscosity was measured. Results are in Table 6.

TABLE 5

Comparison of Turbidity of Essential Oils/Polytrimethylene ether glycol mixtures with Turbidity of Essential Oils/Petrochemical mixtures

| | Essential Oil of Plant (g) | Solvent (g) | Turbidity @ 0 min (NTU) | Turbidity @ 30 min (NTU) | Turbidity @ 120 min (NTU) | Turbidity @ 240 min (NTU) | Turbidity @ 7 days (NTU) | Turbidity @ 14 days (NTU) |
|---|---|---|---|---|---|---|---|---|
| Example | | | | | | | | |
| 13 | Jasmine 0.5 | Polytrimethylene ether glycol (Mn = 650) 9.5 | 7.2 | 5.4 | 4.5 | 4.2 | 4.2 | 3.9 |
| Comp. example | | | | | | | | |
| 4 | Jasmine 0.5 | Hexane 9.5 | 339.4 | 96.6 | 46.7 | 15.9 | 12.1* | 7.7** |
| 5 | Jasmine 0.5 | Dipropylene Glycol 9.5 | 106 | 89 | 96.7 | 98 | 20* | 8.5** |

*Phase separation was observed, particles and dense bottom phase was seen

**Essential oil was dispersible, small drops were visually observed

TABLE 6

Turbidity of Essential Oils/Polytrimethylene ether glycol/water mixtures

| Example | Plant Essential Oil | Solvent | Turbidity @ 0 min (NTU) | Turbidity @ 30 min (NTU) | Turbidity @ 60 min (NTU) | Viscosity (cP) |
|---|---|---|---|---|---|---|
| 14 | Chamomile 0.5 g | Polytrimethylene ether glycol, 9.5 g | 36.8 | 14.5 | 14.7 | 88 @ sp 30 |
| 15 | Chamomile 0.5 g | Polytrimethylene ether glycol, 6.5 g, + Water, 3 g | 119 | 44.3 | 38 | 24 @ sp 60 |
| 16 | Chamomile 0.5 g | Polytrimethylene ether glycol-250, 6.45 g + Water, 3 g + sodium lauryl sulfate, 0.05 g | 248 | 19.1 | 15.3 | 47.8 @ sp 60 |

The results demonstrate that turbidity of mixture of essential oils and polytrimethylene ether glycols were very low, compared to the turbidity with the mixtures containing water. Addition of a small amount of surfactant easily decreased turbidity and a transparent microemulsion was obtained.

Examples 17-19 and Comparative Examples 6-7

1 g of essential oils were mixed with 1 g of polytrimethylene ether glycol (Mn=650). Solubility results are in Table 7.

TABLE 7

Solubility of Essential Oils in Different Solvents

| Example | Essential Oil of Plant | Solvent | Solubility |
|---|---|---|---|
| 17 | 50 wt % Jasmine | Polytrimethylene ether glycol | Miscible |
| 18 | 50 wt % Chamomile | Polytrimethylene ether glycol | Miscible |
| 19 | 50 wt % Lavender | Polytrimethylene ether glycol | Miscible |
| Comparative Example | | | |
| 6 | 15 wt % Jasmine | 1,3-Propanediol | Immiscible |
| 7 | 5 wt % Jasmine | Water | Immiscible |

The results indicate that high concentrations of essential oils of plant materials, compared to polar solvents like propylene glycol and water, can be readily prepared in polytrimethylene ether glycol polymers.

Examples 20-21

0.5 g of essential oils were mixed with 9.5 g of polytrimethylene ether glycol benzoate or laurate. The ester was prepared as it is disclosed in patent U.S. Patent Number 2008/108845, and the molecular weight of the homopolymer was Mn=440. The turbidity of the mixture of essential oil and ester was periodically recorded. Results are in Table 8.

TABLE 8

Turbidity of Essential Oils and Polytrimethylene ether glycol esters

| Example | Essential Oil | Solvent | Turbidity @ 0 hr (NTU) | Turbidity @ 1 hr (NTU) | Turbidity @ 6 hr (NTU) | Turbidity @ 24 hr (NTU) |
|---|---|---|---|---|---|---|
| 20 | 5 wt % Chamomile | Polytrimethylene ether glycol dibenzoate | 37.4 | 2.2 | 2.2 | 2.3 |
| 21 | 5 wt % Chamomile | Polytrimethylene ether glycol laurate | 34.5 | 0.8 | 0.8 | 0.8 |

The mixture of the essential oils and the esters of polytrimethylene ether glycols had very low turbidity within a short period of time after mixing.

What is claimed is:

1. A method for extracting essential oil from a plant comprising:
   a) contacting plant material with a composition comprising one or more of poly(trimethylene ether) glycol homopolymer or copolymer, wherein the homopolymer or copolymer has a number average molecular weight within the range of about 134 to about 2000, to form an extract; and
   b) isolating the extract from the plant material by filtration.

2. The method of claim 1 wherein the molecular weight of the poly(trimethylene ether) glycol homopolymer or copolymer is less than 1000.

3. The method of claim 1, wherein the poly(trimethylene ether) glycol homopolymer or copolymer is renewably sourced.

\* \* \* \* \*